(12) United States Patent
Connolly

(10) Patent No.: US 6,593,090 B2
(45) Date of Patent: *Jul. 15, 2003

(54) HIGH RESOLUTION DNA DETECTION METHODS AND DEVICES

(75) Inventor: Dennis Michael Connolly, Rochester, NY (US)

(73) Assignee: Integrated Nano-Technologies, LLC, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/918,140

(22) Filed: Jul. 30, 2001

(65) Prior Publication Data

US 2002/0182608 A1 Dec. 5, 2002

Related U.S. Application Data

(63) Continuation of application No. 09/545,010, filed on Apr. 7, 2000
(60) Provisional application No. 60/128,149, filed on Apr. 7, 1999.

(51) Int. Cl.⁷ .......................... C12Q 1/68; G01N 15/06; G01N 1/14; G01N 33/53; A61K 38/00
(52) U.S. Cl. .............................. 435/6; 435/7.1; 435/5; 435/7.2; 435/7.9; 435/90; 435/91.1; 422/55; 422/56; 422/58; 422/63; 422/69; 422/76; 436/149; 436/150; 436/806; 436/807; 530/300; 530/350; 530/333; 530/388.1
(58) Field of Search .................. 422/68.1, 50, 55, 422/56, 58, 63, 69, 76; 435/4, 5, 6, 7.1, 7.2; 436/149, 150, 806, 807; 530/300, 350, 333

(56) References Cited

U.S. PATENT DOCUMENTS

| | | | |
|---|---|---|---|
| 5,445,934 A | 8/1995 | Fodor et al. .................... 435/6 |
| 5,653,939 A | 8/1997 | Hollis et al. | |
| 5,739,308 A | 4/1998 | Kandimalla et al. ........ 536/24.5 |
| 5,770,369 A | 6/1998 | Meade et al. | |
| 5,787,032 A | 7/1998 | Heller et al. ................. 365/151 |
| 5,824,473 A | 10/1998 | Meade et al. ................... 435/6 |
| 5,837,546 A | 11/1998 | Allen et al. ................... 436/169 |
| 5,858,659 A | 1/1999 | Sapolsky et al. ............... 435/6 |
| 5,874,046 A | 2/1999 | Megerle ..................... 422/68.1 |
| 5,876,976 A | 3/1999 | Richards et al. ........... 435/91.2 |
| 5,891,630 A | 4/1999 | Eggers et al. .................. 435/6 |
| 6,051,380 A | 4/2000 | Sosnowski et al. ............. 435/6 |
| 6,060,023 A * | 5/2000 | Maracas ..................... 422/68.1 |
| 6,071,699 A | 6/2000 | Meade et al. ................... 435/6 |
| 6,093,370 A | 7/2000 | Yasuda et al. .............. 422/68.1 |
| 6,210,880 B1 * | 4/2001 | Lyamichev ..................... 435/6 |

FOREIGN PATENT DOCUMENTS

| | | |
|---|---|---|
| WO | WO 98/31839 | 7/1998 |
| WO | WO 98/53841 | 12/1998 |
| WO | WO 99/04440 | 1/1999 |
| WO | WO 99/29711 | 6/1999 |
| WO | WO 99/35256 | 7/1999 |
| WO | WO 99/36573 | 7/1999 |
| WO | WO 99/57550 | 11/1999 |
| WO | WO 99/60165 | 11/1999 |
| WO | WO 00/25136 | 5/2000 |

OTHER PUBLICATIONS

Braun et al., "DNA–Templated Assembly and Electrode Attachment of a Conducting Silver Wire," *Nature*, 391:775–778 (1998).
Fink et al., "Electrical Conduction Through DNA Molecules," *Nature*, 398:407–410 (1999).
Chen et al., "Synthesis from DNA of a Molecule with the Connectivity of a Cube, " *Nature*, 350:631–633 (1991).
Mirkin et al., "A DNA–Based Method for Rationally Assembling Nanoparticles into Macroscopic Materials," *Nature*, 382:607–609 (1996).
Alivisatos et al., "Organization of 'Nanocyrstal Molecules' Using DNA,"*Nature*, 382:609–611 (1996).
Braun et al., "DNA–Templated Assembly and Electrode Attachment of a Conducting Silver Wire," *Nature*, 391:775–778 (1998)

\* cited by examiner

*Primary Examiner*—W. Gary Jones
*Assistant Examiner*—Arun Kr. Chakrabarti
(74) *Attorney, Agent, or Firm*—Nixon Peabody LLP

(57) ABSTRACT

The present invention provides methods and devices for detecting a target nucleic acid molecule. A set of oligonucleotide probes integrated into an electric circuit, where the oligonucleotide probes are positioned such that they can not come into contact with one another, are contacted with a sample. If the sample contains a target nucleic acid molecule, one which has sequences complimentary to both probes, the target nucleic acid molecule can bridge the gap between the probes. The resulting bridge can then carry electrical current between the two probes, indicating the presence of the target nucleic acid molecule.

13 Claims, 2 Drawing Sheets

HIGH RESOLUTION DNA DETECTION METHODS AND DEVICES

This application is a Continuation of Ser. No. 09/545,010 filed Apr. 7, 2000 which claims benefit to Provisional Ser. No. 60/128,149 filed Apr. 7, 1999.

BACKGROUND OF THE INVENTION

DNA identification technology has numerous uses including identification of pathogenic organisms, genetic testing, and forensics. Advances have been made to allow for automated screening of thousands of sequences concurrently. Gene chip technologies exist where DNA probes are immobilized on a substrate such as a glass or silicon chip. A sample containing nucleic acid molecules is applied to the chip and the nucleic acid molecules within the sample are allowed to hybridize to the probe DNA on the chip. Fluorescence detection is typically used to identify double stranded nucleic acid molecule products. The advantage of the system is the ability to screen hundreds or thousands of sequences using automated systems.

Hybridization screening with fluorescence detection is a powerful technique for detecting nucleic acid sequences. However, in order to detect target DNA molecules, the target must first be amplified by PCR to get a reliable signal. The gene chip technology also requires a system capable of detecting fluorescent or radioactive materials. Such a system is expensive to use and is not amenable to a portable system for biological sample detection and identification. Furthermore, the hybridization reactions take up to two hours. For many potential uses, such as detecting biological warfare agents, the gene chip system is simply not effective. Therefore, there is a need for a system which can rapidly detect small quantities of a target nucleic acid molecule without relying on PCR amplification.

SUMMARY OF THE INVENTION

The present invention provides a method for detecting a target nucleic acid molecule. A device for detecting the presence of a target nucleic acid molecule is provided having two electronic leads, where the ends of the leads are located near each other but are not in contact. One or more sets of two oligonucleotide probes are attached to the electronic leads. The oligonucleotide probes are positioned such that the probes can not come into contact with one another and such that a target nucleic acid molecule, which has two sequences complimentary to the probes can bind to both probes concurrently. A sample which may have the target nucleic acid molecule is contacted with the probes under selective hybridization conditions. If the target is present it bridges the gap between the probes. The target nucleic acid molecule may then carry current between the probes, or be used as a support to form a conductive wire between the two probes.

The present invention also provides a device for detecting the presence of a target nucleic acid molecule. The device has two electronic leads, where the ends of the leads are located near each other but are not in contact. One or more sets of two oligonucleotide probes are attached to the electronic leads. The oligonucleotide probes are positioned such that the probes can not come into contact with one another and such that a target nucleic acid molecule, which has two sequences complimentary to the probes can bind to both probes concurrently.

DETAILED DESCRIPTION OF THE INVENTION

Figure 1A:
FIG. 1 graphically depicts the method of the present invention. Two leads are provided each having a probe which is complimentary to sequences on a target nucleic acid molecule (FIG. 1A). A target nucleic acid molecule binds to the two probes at the complimentary sequences (FIG. 1B). The complimentary strand is filled in (FIG. 1C). Nucleases are used to remove the free ends of the target nucleic acid molecule (FIG. 1D). Current can be passed through the double stranded molecule or the target nucleic acid molecule and probes may be coated with a conductor and then tested for current flow.
Figure 1C:
Figure 1B:
Figure 1D:
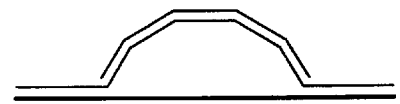

The present invention provides devices and methods for rapidly detecting the presence of nucleic acid molecules. The target nucleic acid molecule either itself, or as a support, is used to complete a electrical circuit. The presence of the target nucleic acid molecule is indicated by the ability to conduct an electrical signal through the circuit. In the case where the target nucleic acid molecule is not present, the circuit is not be completed. Thus, the target nucleic acid molecule acts as a switch. The presence of the nucleic acid molecule provides an on signal for an electrical circuit, whereas the lack of the target nucleotide is interpreted as an off signal. Due to the direct detection of the target nucleic acid molecule, the method allows for extremely sensitive detection of target molecules connect two wires.

The detection device is constructed on a support. Examples of useful substrate materials include, e.g., glass, quartz and silicon as well as polymeric substrates, e.g. plastics. In the case of conductive or semi-conductive substrates, it will generally be desirable to include an insulating layer on the substrate. However, any solid support which has a non-conductive surface may be used to construct the device. The support surface need not be flat. In fact, the support may be on the walls of a chamber in a chip.

Two leads are provided having ends located close together, within the spanning distance of a target nucleic acid molecule, but not contacting one another. Current can not flow effectively between the leads without the presence of a target nucleic acid molecule to bridge the two leads. Two probes specific to the target nucleic acid molecule are used. The first is attached to one lead, the second to the other lead. The two probes are specific to sequences on the target molecule which are separated by sufficient distance to span the region between the leads. Typically, the gap will by in micron or fractions of microns in length. However, as chip manufacturing has improved, it has become possible to shrink the distance between elements on a chip, requireing shorter lengths of target nucleic acid molecules.

The target nucleic acid molecule is passed over the two leads. If a target molecule has a sequence complimentary to one of the probes, it can bind to that probe. Once bound to that probe, the nucleic acid molecule is tethered at that site. The sequence complimentary to the second probe can then bind to the second probe. To facilitate such a reaction, the two complimentary sequences should be chosen such that the length of the molecule in between can span the distance between the two leads and provide flexibility for the nucleic acid molecule to move easily, such that the second complimentary sequence readily binds to the second probe.

In a preferred embodiment, the probes are selected to bind with the target such that they have approximately the same melting temperature. This can be done by varying the lengths of the hybridization region. A-T rich regions may have longer target sequences, whereas G-C rich regions would have shorter target sequences.

Hybridization assays on substrate-bound oligonucleotide arrays involve a hybridization step and a detection step. In the hybridization step, a hybridization mixture containing the target and an isostabilizing agent, denaturing agent or renaturation accelerant is brought into contact with the probes of the array and incubated at a temperature and for a time appropriate to allow hybridization between the target and any complementary probes. Usually, unbound target molecules are then removed from the array by washing with a wash mixture that does not contain the target, such as hybridization buffer. This leaves only bound target molecules. In the detection step, the probes to which the target has hybridized are identified. In the present method the detection is carried out by detecting a completed electronic circuit. Since the nucleotide sequence of the probes at each feature is known, identifying the locations at which target has bound provides information about the particular sequences of these probes.

Including a hybridization optimizing agent in the hybridization mixture significantly improves signal discrimination between perfectly matched targets and single-base mismatches. As used herein, the term "hybridization optimizing agent" refers to a composition that decreases hybridization between mismatched nucleic acid molecules, i.e., nucleic acid molecules whose sequences are not exactly complementary.

An isostabilizing agent is a composition that reduces the base-pair composition dependence of DNA thermal melting transitions. More particularly, the term refers to compounds that, in proper concentration, result in a differential melting temperature of no more than about 1° C. for double stranded DNA oligonucleotides composed of AT or GC, respectively. Isostabilizing agents preferably are used at a concentration between 1 M and 10 M, between 2 M and 6 M, between 4 M and 6 M, between 4 M and 10 M and, optimally, at about 5 M. For example, 5 M agent in 2×SSPE is suitable. Betaines and lower tetraalkyl ammonium salts are examples of isostabilizing agents. In one embodiment, the isostabilizing agent is not an alkylammonium ion.

Betaine (N,N,N,-trimethylglycine; (Rees et al., *Biochem.*, (1993) 32:137–144), which is hereby incorporated by reference) can eliminate the base pair composition dependence of DNA thermal stability. Unlike TMACl, betaine is zwitterionic at neutral pH and does not alter the polyelectrolyte behavior of nucleic acids while it does alter the composition-dependent stability of nucleic acids. Inclusion of betaine at about 5 M can lower the average hybridization signal, but increases the discrimination between matched and mismatched probes.

A denaturing agent is a compositions that lowers the melting temperature of double stranded nucleic acid molecules by interfering with hydrogen bonding between bases in a double-stranded nucleic acid or the hydration of nucleic acid molecules. Denaturing agents can be included in hybridization buffers at concentrations of about 1 M to about 6 M and, preferably, about 3 M to about 5.5 M.

Denaturing agents include formamide, formaldehyde, DMSO ("dimethylsulfoxide"), tetraethyl acetate, urea, GuSCN, glycerol and chaotropic salts. As used herein, the term "chaotropic salt" refers to salts that function to disrupt van der Waal's attractions between atoms in nucleic acid molecules. Chaotropic salts include, for example, sodium trifluoroacetate, sodium tricholoroacetate, sodium perchlorate, guanidine thiocyanate ("GuSCN"), and potassium thiocyanate.

A renaturation accelerant is a compound that increases the speed of renaturation of nucleic acids by at least 100-fold. They generally have relatively unstructured polymeric domains that weakly associate with nucleic acid molecules. Accelerants include heterogenous nuclear ribonucleoprotein ("hnRP") A1 and cationic detergents such as, preferably, CTAB ("cetyltrimethylammonium bromide") and DTAB ("dodecyl trimethylammonium bromide"), and, also, polylysine, spermine, spermidine, single stranded binding protein ("SSB"), phage T4 gene 32 protein and a mixture of ammonium acetate and ethanol. Renaturation accelerants can be included in hybridization mixtures at concentrations of about 1 mu M to about 10 mM and, preferably, 1 mu M to about 1 mM. The CTAB buffers work well at concentrations as low as 0.1 mM.

Homologous nucleotide sequences can be detected by selectively hybridizing to each other. Selectively hybridizing is used herein to mean hybridization of DNA or RNA probes from one sequence to the "homologous" sequence under stringent or non-stringent conditions (Ausubel, et al., Eds., 1989, Current Protocols in Molecular Biology, Vol. I, Greene Publishing Associates, Inc. and John Wiley & Sons, Inc., New York, at page 2.10.3, which is hereby incorporated by reference). Hybridization and wash conditions are also exemplified in Sambrook, et al., Molecular Cloning: A Laboratory Manual, Second Edition, Cold Spring Harbor, N.Y., (1989), which is hereby incorporated by reference.

A variety of hybridization buffers are useful for the hybridization assays of the invention. Addition of small amounts of ionic detergents (such as N-lauroyl-sarkosine) are useful. LiCl is preferred to NaCl. Hybridization can be at 20°–65° C., usually 37° C. to 45° C. for probes of about 14 nucleotides. Additional examples of hybridization conditions are provided in several sources, including: Sambrook et al., Molecular Cloning: A Laboratory Manual (1989), 2 nd Ed., Cold Spring Harbor, N.Y.; and Berger and Kimmel, "Guide to Molecular Cloning Techniques," *Methods in Enzymology*, (1987), Volume 152, Academic Press, Inc., San Diego, Calif.; Young and Davis, *Proc. Natl. Acad. Sci. USA*, 80:1194 (1983), which are hereby incorporated by reference.

In addition to aqueous buffers, non-aqueous buffers may also be used. In particular non-aqueous buffers which facilitate hybridization but have low electrical conductivity are preferred.

The hybridization mixture is placed in contact with the array and incubated. Contact can take place in any suitable container, for example, a dish or a cell specially designed to hold the probe array and to allow introduction of the fluid into and removal of it from the cell so as to contact the array. Generally, incubation will be at temperatures normally used for hybridization of nucleic acids, for example, between about 20° C. and about 75° C., e.g., about 25° C., about 30° C., about 35° C., about 40° C., about 45° C., about 50° C., about 55° C., about 60° C. or about 65° C. For probes longer than about 14 nucleotides, 37° C.–45° C. is preferred. For shorter probes, 55° C.–65° C. is preferred. More specific hybridization conditions can be calculated using formulas for determining the melting point of the hybridized region. Preferably, hybridization is carried out at a temperature at or between ten degrees below the melting temperature and the melting temperature. More preferred, the hybridization is carried out at a temperature at or between five degrees below the melting temperature and the melting temperature. The target is incubated with the probe array for a time sufficient to allow the desired level of hybridization between the target and any complementary probes in the array. After incubation with the hybridization mixture, the array usually is washed with the hybridization buffer, which also can include the hybridization optimizing agent. These agents can be included in the same range of amounts as for the hybridization step, or they can be eliminated altogether. Then the array can be examined to identify the probes to which the target has hybridized.

The target polynucleotide whose sequence is to be determined is usually isolated from a tissue sample. If the target is genomic, the sample may be from any tissue (except exclusively red blood cells). For example, whole blood, peripheral blood lymphocytes or PBMC, skin, hair or semen are convenient sources of clinical samples. These sources are also suitable if the target is RNA. Blood and other body fluids are also a convenient source for isolating viral nucleic acids. If the target is mRNA, the sample is obtained from a tissue in which the mRNA is expressed. If the polynucleotide in the sample is RNA, it may be reverse transcribed to DNA, but in this method need not be converted to DNA.

Various methods exist for attaching the probes to the electronic circuit. For example, U.S. Pat. Nos. 5,861,242; 5,861,242; 5,856,174; 5,856,101; and 5,837,832, which are hereby incorporated by reference, disclose a method where light is shone through a mask to activate functional (for oligonucleotides, typically an —OH) groups protected with a photo-removable protecting group on a surface of a solid support. After light activation, a nucleoside building block, itself protected with a photo-removable protecting group (at the 5'-OH), is coupled to the activated areas of the support. The process can be repeated, using different masks or mask orientations and building blocks, to place probes on a substrate.

Alternatively, new methods for the combinatorial chemical synthesis of peptide, polycarbamate, and oligonucleotide arrays have recently been reported (see Fodor et al., *Science*, 251:767–773 (1991); Cho et al., *Science*, 261:1303–1305 (1993); and Southern et al., *Genomics* 13:1008–10017 (1992), which are hereby incorporated by reference). These arrays, or biological chips (see Fodor et al., *Nature*, 364:555–556 (1993), which is hereby incorporated herein by reference), harbor specific chemical compounds at precise locations in a highdensity, information rich format, and are a powerful tool for the study of biological recognition processes.

Preferably, the probes are attached to the leads through spatially directed oligonucleotide synthesis. Spatially directed oligonucleotide synthesis may be carried out by any method of directing the synthesis of an oligonucleotide to a specific location on a substrate. Methods for spatially directed oligonucleotide synthesis include, without limitation, light-directed oligonucleotide synthesis, microlithography, application by ink jet, microchannel deposition to specific locations and sequestration with physical barriers. In general these methods involve generating active sites, usually by removing protective groups; and coupling to the active site a nucleotide which, itself, optionally has a protected active site if further nucleotide coupling is desired.

In one embodiment the lead-bound oligonucleotides are synthesized at specific locations by light-directed oligonucleotide synthesis which is disclosed in U.S. Pat. No. 5,143,854; PCT application WO 92/10092; and PCT application WO 90/15070. In a basic strategy of this process, the surface of a solid support modified with linkers and photolabile protecting groups is illuminated through a photolithographic mask, yielding reactive hydroxyl groups in the illuminated regions. A 3'-O-phosphoramidite-activated deoxynucleoside (protected at the 5'-hydroxyl with a photolabile group) is then presented to the surface and coupling occurs at sites that were exposed to light. Following the optional capping of unreacted active sites and oxidation, the substrate is rinsed and the surface is illuminated through a second mask, to expose additional hydroxyl groups for coupling to the linker. A second 5'-protected, 3'-O-phosphoramidite-activated deoxynucleoside (C-X) is presented to the surface. The selective photodeprotection and coupling cycles are repeated until the desired set of probes are obtained. Photolabile groups are then optionally removed and the sequence is, thereafter, optionally capped. Side chain protective groups, if present, are also removed. Since photolithography is used, the process can be miniaturized to specifically target leads in high densities on the support.

This general process can be modified. For example, the nucleotides can be natural nucleotides, chemically modified nucleotides or nucleotide analogs, as long as they have activated hydroxyl groups compatible with the linking chemistry. The protective groups can, themselves, be photolabile. Alternatively, the protective groups can be labile under certain chemical conditions, e.g., acid. In this example, the surface of the solid support can contain a composition that generates acids upon exposure to light. Thus, exposure of a region of the substrate to light generates acids in that region that remove the protective groups in the exposed region. Also, the synthesis method can use 3'-protected 5'-O-phosphoramidite-activated deoxynucleoside. In this case, the oligonucleotide is synthesized in the 5' to 3' direction, which results in a free 5' end.

The general process of removing protective groups by exposure to light, coupling nucleotides (optionally competent for further coupling) to the exposed active sites, and optionally capping unreacted sites is referred to herein as "light-directed nucleotide coupling."

The probe molecules can be targeted to the leads through chemical and electrical methods. The probes may be targeted to the leads by using a chemical reaction for attaching the probe or nucleotide to the lead which preferably binds the probe or nucleotide to the lead rather than the support material. Alternatively, the probe or nucleotide may be targeted to the lead by building up a charge on the lead which electrostatically attracts the probe or nucleotide.

Nucleases can be used to remove probes which are attached to the chip or lead in the wrong position. More particularly, a target nucleic acid molecule may be added to the probes. Targets which bind at both ends to probes, one end to each lead, will have no free ends and will be resistant to exonuclease digestion. However, probes which are positioned so that the target can not contact both leads will be bound only one end, leaving the molecule subject to digestion. Thus, improperly located probes can be removed while protecting the properly located probes. After the protease is removed or inactivated the target nucleic acid molecule can be removed and the device is ready for use.

Interest has been growing in the fabrication of microfluidic devices. Typically, advances in the semiconductor manufacturing arts have been translated to the fabrication of micromechanical structures, e.g., micropumps, microvalves and the like, and microfluidic devices including miniature chambers and flow passages.

A number of researchers have attempted employ these microfabrication techniques in the miniaturization of some of the processes involved in genetic analysis in particular. For example, published PCT Application No. WO 94/05414, to Northrup and White, incorporated herein by reference in its entirety for all purposes, reports an integrated micro-PCR apparatus for collection and amplification of nucleic acids from a specimen. U.S. Pat. No. 5,304,487 to Wilding et al., and U.S. Pat. No. 5,296,375 to Kricka et al., discuss devices for collection and analysis of cell containing samples. Similar techniques can be used to produce chips which can accept a sample, release the nucleic acid molecules and then detect the target sequences.

Micorfluidic devices are disclosed in U.S. Pat. No. 6,046,056, which is hereby incorporated by reference. The devices includes a series of channels fabricated into the surface of the substrate. At least one of these channels will typically have very small cross sectional dimensions, e.g., in the range of from about 0.1 $\mu$m to about 500 $\mu$m. Preferably the cross-sectional dimensions of the channels will be in the range of from about 0.1 to about 200 $\mu$m and more preferably in the range of from about 0.1 to about 100 $\mu$m. In particularly preferred aspects, each of the channels will have at least one cross-sectional dimension in the range of from about 0.1 $\mu$m to about 100 $\mu$m. Although generally shown as straight channels, it will be appreciated that in order to maximize the use of space on a substrate, serpentine, saw tooth or other channel geometries, to incorporate effectively longer channels in shorter distances.

Manufacturing of these microscale elements into the surface of the substrates may generally be carried out by any number of microfabrication techniques that are well known in the art. For example, lithographic techniques may be employed in fabricating, e.g., glass, quartz or silicon substrates, using methods well known in the semi-conductor manufacturing industries such as photolithographic etching, plasma etching or wet chemical etching. Alternatively, micromachining methods such as laser drilling, micromilling and the like may be employed.

Similarly, for polymeric substrates, well known manufacturing techniques may also be used. These techniques include injection molding or stamp molding methods where large numbers of substrates may be produced using, e.g., rolling stamps to produce large sheets of microscale substrates or polymer microcasting techniques where the substrate is polymerized within a micromachined mold.

The devices will typically include an additional planar element which overlays the channeled substrate enclosing and fluidly sealing the various channels to form conduits. Attaching the planar cover element may be achieved by a variety of means, including, e.g., thermal bonding, adhesives or, in the case of certain substrates, e.g., glass, or semi-rigid and non-rigid polymeric substrates, a natural adhesion between the two components. The planar cover element may additionally be provided with access ports and/or reservoirs for introducing the various fluid elements needed for a particular screen.

The device may also include reservoirs disposed and fluidly connected at the ends of the channels. A sample channel is used to introduce the test compounds into the device. The introduction of a number of individual, discrete volumes of compounds into the sample may be carried out by a number of methods. For example, micropipettors may be used to introduce the test compounds into the device. In preferred aspects, an electropipettor may be used which is fluidly connected to sample channel. Generally, an electropipettor utilizes electroosmotic fluid direction, to alternately sample a number of test compounds, or subject materials, and spacer compounds. The pipettor then delivers individual, physically isolated samples into the sample channel for subsequent manipulation within the device.

Alternatively, the sample channel may be individually fluidly connected to a plurality of separate reservoirs via separate channels. The separate reservoirs each contain a reactant compound, such as proteins or detergents, with additional reservoirs being provided for appropriate spacer compounds. The test compounds, reactant compounds, and/or spacer compounds are then transported from the various reservoirs into the sample channels using appropriate fluid direction schemes.

The sample collection portion of a device of the present invention, whether or not on a micro scale, generally provides for the identification of the sample, while preventing contamination of the sample by external elements, or contamination of the environment by the sample. Generally, this is carried out by introducing a sample for analysis, e.g., preamplified sample, tissue, blood, saliva, etc., directly into a sample collection chamber within the device. Typically, the prevention of cross-contamination of the sample may be accomplished by directly injecting the sample into the sample collection chamber through a sealable opening, e.g., an injection valve, or a septum. Generally, sealable valves are preferred to reduce any potential threat of leakage during or after sample injection. Alternatively, the device may be provided with a hypodermic needle integrated within the device and connected to the sample collection chamber, for direct acquisition of the sample into the sample chamber. This can substantially reduce the opportunity for contamination of the sample.

In addition to the foregoing, the sample collection portion of the device may also include reagents and/or treatments for neutralization of infectious agents, stabilization of the specimen or sample, pH adjustments, and the like. Stabilization and pH adjustment treatments may include, e.g., introduction of heparin to prevent clotting of blood samples, addition of buffering agents, addition of protease or nuclease inhibitors, preservatives and the like. Such reagents may generally be stored within the sample collection chamber of the device or may be stored within a separately accessible chamber, wherein the reagents may be added to or mixed with the sample upon introduction of the sample into the device. These reagents may be incorporated within the device in either liquid or lyophilized form, depending upon the nature and stability of the particular reagent used.

For those embodiments where whole cells, viruses or other tissue samples are being analyzed, it will typically be necessary to extract the nucleic acids from the cells or viruses, prior to continuing with the various sample preparation operations. Accordingly, following sample collection, nucleic acids may be liberated from the collected cells, viral coat, etc., into a crude extract, followed by additional treatments to prepare the sample for subsequent operations, e.g., denaturation of contaminating (DNA binding) proteins, purification, filtration, desalting, and the like.

Liberation of nucleic acids from the sample cells or viruses, and denaturation of DNA binding proteins may generally be performed by physical or chemical methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins. Generally, where chemical extraction and/or denaturation methods are used, the appropriate reagents may be incorporated within the extraction chamber, a separate accessible chamber or externally introduced.

Alternatively, physical methods may be used to extract the nucleic acids and denature DNA binding proteins. U.S. Pat. No. 5,304,487, herein incorporated by reference, discusses the use of physical protrusions within microchannels or sharp edged particles within a chamber or channel to pierce cell membranes and extract their contents. More traditional methods of cell extraction may also be used, e.g., employing a channel with restricted cross-sectional dimension which causes cell lysis when the sample is passed through the channel with sufficient flow pressure. Alternatively, cell extraction and denaturing of contaminating proteins may be carried out by applying an alternating electrical current to the sample. More specifically, the sample of cells is flowed through a microtubular array while an alternating electric current is applied across the fluid flow. A variety of other methods may be utilized within the device of the present invention to effect cell lysis/extraction, including, e.g., subjecting cells to ultrasonic agitation, or forcing cells through microgeometry apertures, thereby subjecting the cells to high shear stress resulting in rupture.

Following extraction, it will often be desirable to separate the nucleic acids from other elements of the crude extract, e.g., denatured proteins, cell membrane particles, and the like. Removal of particulate matter is generally accomplished by filtration, flocculation or the like. A variety of filter types may be readily incorporated into the device. Further, where chemical denaturing methods are used, it may be desirable to desalt the sample prior to proceeding to the next step. Desalting of the sample, and isolation of the nucleic acid may generally be carried out in a single step, e.g., by binding the nucleic acids to a solid phase and washing away the contaminating salts or performing gel filtration chromatography on the sample. Suitable solid supports for nucleic acid binding include, e.g., diatomaceous earth, silica, or the like. Suitable gel exclusion media is also well known in the art and is commercially available from, e.g., Pharmacia and Sigma Chemical. This isolation and/or gel filtration/desalting may be carried out in an additional chamber, or alternatively, the particular chromatographic media may be incorporated in a channel or fluid passage leading to a subsequent reaction chamber.

Alternatively, the interior surfaces of one or more fluid passages or chambers may themselves be derivatized to provide functional groups appropriate for the desired purification, e.g., charged groups, affinity binding groups and the like.

In a preferred embodiment of the invention, ligation methods may be used to specifically identify single base differences in sequences. Previously, methods of identifying known target sequences by probe ligation methods have been reported. U.S. Pat. No. 4,883,750 to N. M. Whiteley et al.; D. Y. Wu et al., *Genomics*, 4:560 (1989); U. Landegren et al., *Science*, 241:1077 (1988); and E. Winn-Deen et al., *Clin. Chem.*, 37:1522 (1991), which are hereby incorporated by reference. In one approach, known as oligonucleotide ligation assay ("OLA"), two probes or probe elements which span a target region of interest are hybridized to the target region. Where the probe elements basepair with adjacent target bases, the confronting ends of the probe elements can be joined by ligation, e.g., by treatment with ligase. The ligated probe element is then assayed, evidencing the presence of the target sequence.

In the present invention, one or both probes may be designed to specifically recognize a variation in the sequence at the end of the probe. After the target binds to the probes, the target is treated with nucleases to remove the ends of the molecules which do not bind to the probes. The junction is then treated with ligase. If the complimentary sequence is present at the end of the probe, the ligase will ligate the target to the probe. The test chamber can then be heated up to denature non-ligated targets. Detection of the specific target can then be carried out.

In one embodiment of the invention, the probe set is contacted with a target nucleic acid molecule and after hybridization the nucleic acid molecules are coated with a conductor, such as a metal, as described in U.S. patent applications Ser. Nos. 60/095,096, 60/099,506, or 09/315,750 which are hereby incorporated by reference. The coated nucleic acid molecule can then conduct electricity across the gap between the pair of probes, thus producing a detectable signal indicative of the presence of a target nucleic acid molecule.

Braun demonstrated that silver could be deposited along a DNA molecule. A three-step process is used. First, silver is selectively localized to the DNA molecule through a Ag+/Na+ ion-exchange (Barton, in Bioinorganic Chemistry (eds Bertini, et al.) ch. 8 (University Science Books, Mill Valley, 1994, which is hereby incorporated by reference) and complexes are formed between the silver and the DNA bases (Spiro (ed.) Nucleic Acid-Metal Ion Interactions (Wiley Interscience, New York 1980; Marzeilli, et al., J. Am. Chem. Soc. 99:2797 (1977); Eichorn (ed.) Inorganic Biochemistry, Vol. 2, ch 33–34 (Elsevier, Amsterdam, 1973), which are hereby incorporated by reference). The ion-exchange process may be monitored by following the quenching of the fluorescence signal of the labeled DNA.. The silver ion-exchanged DNA is then reduced to form aggregates with bound to the DNA skeleton. The silver aggregates are further developed using standard procedures, such as those used in photographic chemistry (Holgate, et al., J. Histochem. Cytochem. 31:938 (1983); Birell, et al., J. Histochem. Cytochem. 34:339 (1986), which are hereby incorporated by reference).

The nucleic acid molecule itself may have some conductive properties of its own. These properties may be modified to reduce any detrimental effects on the function of the electronic circuit (Meade, et al, U.S. Pat. No. 5,770,369, "Nucleic Acid Mediated Electron Transfer" (1998), which is hereby incorporated by reference). Modification of the electrical properties of the nucleic acid molecule may be made by intercalating compounds between the bases of the nucleic acid molecule, modifying the sugar-phosphate backbone, or by cleaving the nucleic acid molecule after the circuit elements are formed. Cleavage of the nucleic acid molecule may be accomplished by irradiation, chemical treatment, or enzymatic degradation. Irradiation using gamma-radiation is preferred because radiation may penetrate materials coating the nucleic acid molecule.

In another aspect of the invention, the electrical conductivity of nucleic acid molecules is relied upon to transmit the electrical signal. Hans-Werner Fink and Christian Schoenenberger reported in Nature (1999), which is hereby incorporated by reference, that double-stranded DNA conducts electricity like a semiconductor. This flow of current can be sufficient to construct a simple switch. The present invention provides an electronic detector based upon such a nucleic acid switch, which will indicate whether or not a target nucleic acid molecule is present within a sample.

Probes to the target nucleic acid molecule are immobilized within an electrical circuit. The probes are physically located at a distance sufficient that they can not come into contact with one another. The sample to be tested is contacted with the probes. If a nucleic acid molecule is present in the sample which has sequences homologous or complementary to the two probes, the nucleic acid molecule can bridge the gap between the probes. The detection unit can then detect an electrical current which can flow through the nucleic acid molecule. A computer unit can detect the presence of the nucleic acid molecule as an "on" switch, while an unbridged probe set would be an "off" switch. The information is processed by a digital computer which correlates the status of the switch with the presence of a particular target. The computer can also analyze the results from several switches specific for the same target, to determine specificity of binding and target concentration. The information could be quickly identified to the user by indicating the presence or absence of the biological material, organism, mutation, or other target of interest on the nucleic acid molecule.

A detection device could comprise numerous different probe sets which could detect a wide variety of targets. Thus a detection device could screen for multiple target DNA molecules. For example, a detection device could have probe sets directed at multiple pathogenic organisms. In that way, a sample could be screened for several pathogens simultaneously. Each probe set would be a separate switch which would indicate the presence or absence of the complimentary nucleic acid molecule.

A cell sample can be prepared by either chemical (including enzymatic) or physical disruption, or a combination thereof. After lysis the sample can be further processed. For example, the sample can be treated with RNase to remove any RNA to limit detection to DNA.

Prior to or at the point of contact with the probes, the nucleic acid molecules in the sample are denatured. Denaturation is preferentially carried out by heat treatment. Denaturation can also be carried out by varying the ionic concentration of the carrier solution or by a combination of ionic and heat treatment.

The present invention also has the advantage of being used for multiple samples. The probe sets can be recycled by stripping the target DNAs from the probe sets. In a preferred embodiment the stripping is accomplished by increasing temperature and/or salt concentration. The probe set is then ready for analysis of an additional sample.

The nucleic acid molecule of the present invention is preferentially a DNA or RNA molecule. In the present invention, preferred nucleic acid molecules include RNA and DNA. RNA detection may allow for more sensitivity since RNA transcripts may be at higher levels. Also included within the invention are chemically modified nucleic acid molecules or nucleic acid analogs. Such RNA or DNA analogs comprise but are not limited to 2'-O-alkyl sugar modifications, methylphosphonate, phosphorothioate, phosphorodithioate, formacetal, 3'-thioformacetal, sulfone, sulfamate, and nitroxide backbone modifications, amides, and analogs wherein the base moieties have been modified. In addition, analogs of oligomers may be polymers in which the sugar moiety has been modified or replaced by another suitable moiety, resulting in polymers which include, but are not limited to, polyvinyl backbones (Pitha et al., "Preparation and Properties of Poly (I-vinylcytosine)," *Biochim. Biophys. Acta*, 204:381–8 (1970); Pitha et al., "Poly(1-vinyluracil): The Preparation and Interactions with Adenosine Derivatives," *Biochim. Biophys. Acta*, 204:39–48 (1970), which are hereby incorporated by reference), morpholino backbones (Summerton, et al., "Morpholino Antisense Oligomers: Design, Preparation, and Properties," *Antisense Nucleic Acid Drug Dev.*, 7:187–9 (1997), which is hereby incorporated by reference) and peptide nucleic acid (PNA) analogs (Stein et al., "A Specificity Comparison of Four Antisense Types: Morpholino, 2'-O-methyl RNA, DNA, and Phosphorothioate DNA," *J. Antisense Nucleic Acid Drug Dev.*, 7:151–7 (1997); Egholm et al., "Peptide Nucleic Acids (PNA)-Oligonucleotide Analogues with an Achiral Peptide Backbone," *J. Am. Chem. Soc.*, 114:1895–1897 (1992); Faruqi et al., "Peptide Nucleic Acid-Targeted Mutagenesis of a Chromosomal Gene in Mouse Cells," *Proc. Natl. Acad. Sci. USA*, 95:1398–403 (1998); Christensen et al., "Solid-Phase Synthesis of Peptide Nucleic Acids," *J. Pept. Sci.*, 1:175–83 (1995); Nielsen et al., "Peptide Nucleic Acid (PNA). A DNA Mimic with a Peptide Backbone," *Bioconjug. Chem.*, 5:3–7 (1994), which are hereby incorporated by reference). In addition linkages may contain the following exemplary modifications: pendant moieties, such as, proteins (including, for example, nucleases, toxins, antibodies, signal peptides and poly-L-lysine); intercalators (e.g., acridine and psoralen), chelators (e.g., metals, radioactive metals, boron and oxidative metals), alkylators, and other modified linkages (e.g., alpha anomeric nucleic acids). Such analogs include various combinations of the above-mentioned modifications involving linkage groups and/or structural modifications of the sugar or base for the purpose of improving RNAseH-mediated destruction of the targeted RNA, binding affinity, nuclease resistance, and or target specificity.

In one embodiment, the bridging nucleic acid molecule can be made double stranded by adding a segment of a nucleic acid molecule which is complimentary to the region of the target nucleic acid molecule located between the sequences complimentary to the probes. Ligase can be used to ligate the fragments into one molecule. The device may be recycled by passing through a restriction endonuclease to release the bridging nucleic acid molecule. Alternatively, a polymerase can be used to fill in the complimentary sequence. In that case, the solution must contain nucleotides for the synthesis of the complimentary strand.

Each probe set consists of two probes. Each probe may consist of one or more copies of the oligonucleotide, where all the copies for that probe attach to the circuit so that electrical current can be carried through the probe and to the circuit. A connection between any of the oligonucleotides in one probe with any of the oligonucleotides in the other probe of the set will complete the circuit. producing an "on" signal. If the probes consist of multiple copies of the oligonucleotides and/or if multiple probes are used, the device can be used to quantitate the level of the target nucleic acid molecule in the sample, by the signal strength or the number of activated switches.

The number of probes may be increased in order to determine concentrations of the target nucleic acid molecule. For example, several thousand repeated probes may be produced in the detection unit. The circuit would be able to count the number of occupied sites. Calculations could be done by the unit to determine the concentration of the target molecule.

The present invention can be used for numerous applications, such as detection of pathogens. For example, samples may be isolated from drinking water or food and rapidly screened for infectious organisms. This invention may also be used for DNA sequencing using hybridization techniques. Such methods are described in U.S. Pat. No. 5,837,832, which is hereby incorporated by reference. The present invention may be used to screen for mutations or polymorphisms in samples isolated from patients.

The present invention may also be used for food and water testing. In recent times, there have been several large recalls of tainted meat products. The electronic DNA detection system can be used for the in-process detection of pathogens in foods and the subsequent disposal of the contaminated materials. This could significantly improve food safety, prevent food borne illnesses and death, and avoid costly recalls. Chips with probes that can identify common food borne pathogens, such as *Salmonella* and *E. Coli.*, could be designed for use within the food industry.

In yet another embodiment, the present invention can be used for real time detection of biological warfare agents: With the recent concerns of the use of biological weapons in a theater of war and in terrorist attacks, the device could be configured into a personal sensor for the combat soldier or into a remote sensor for advanced warnings of a biological threat. The devices which can be used to specifically identity of the agent, can be coupled with a modem to send the information to another location. Mobile devices may also include a global positioning system to provide both location and pathogen information.

In yet another embodiment, the present invention may be used to identify an individual. A series of probes, of sufficient number to distinguish individuals with a high degree of reliability, are placed within the device. Various polymorphism sites are used. Preferentially, the device can determine the identity to a specificity of greater than one in 1 million, more preferred is a specificity of greater than one in one billion, even more preferred is a specificity of greater than one in ten billion.

As an example, a flow chart is provided indicating how a cell sample can be tested for the presence of a target nucleic acid molecule:

1. Inject sample
2. Lyse cells
3. Process lysate
4. Denature nucleic acid molecules
4. Contact sample with probe sets—under stringent conditions
5. Determine whether current can travel between a probe set
6. Correlate the current signal with a positive identification of the target DNA Note that not all steps are required depending upon the application. For example, lysis is only needed if the DNA is still within a cell.

Control probe sets can be utilized to verify that the system is working appropriately. The probe sets can recognize sequences known to occur with in the sample or be nucleic acid molecules which are added to the sample.

Controls are especially useful to determine the presence of sequences having a polymorphism. Control nucleic acid molecules lacking the polymorphism may be compared in a separate test. In a preferred embodiment, the control sequence is tested at the same time in a separate chamber in the device. The correct control sequence will hybridize to the probes at a slightly higher temperature. This difference can be used to differentiate the single base mutant from the correct sequence. The device will indicate binding by the correct sequence at a temperature where the mutant sequence can not bind. However, at a lower temperature, both sequences will bind.

Figure 2A:
FIGS. 2A–E show a variation on the method shown in FIG. 1 using a ligase method to distinguish a single base variation. The variation is identified by the asterisks in FIGS. 2C–D. After step D, a ligase is used. Only those targets which have an exact match at the ends of the probes will ligate. After ligation, the sample is heated to remove non-ligated target molecules (FIG. 2E). The structure in FIG. 2E is stable at higher temperatures, whereas the un-ligated structure in FIG. 2D would denature under heat treatment.
Figure 2C:
Figure 2B:
Figure 2D:
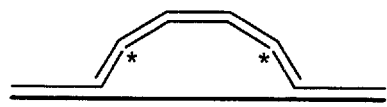
Figure 2E:
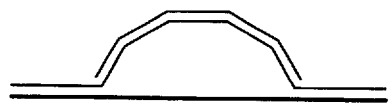

In yet another embodiment, the nucleotide probes on the substrate may be randomly chosen. A linker nucleic acid molecule comprising a complimentary sequence to the substrate bound probe and a sequence complimentary to the target nucleic acid molecule (See FIGS. 2C–D). Thus the linker can be used to make the probe sequence able to detect any target nucleic acid sequence without having to modify the device itself. Rather the linker molecule may be bound to the substrate bound nucleic acid molecule either before or together with the sample to be tested. If desired the linker may be ligated to the substrate bound probe. This would allow for the reuse of the linker with multiple samples.

The present invention can be used to monitor gene expression in cells. The level of RNA is determined using multiple switches with probes complimentary to the target RNA molecule. Samples can be taken at various times after a stimulus or at different stages of development.

In yet another embodiment, the present invention can be used to sequence nucleic acid molecules. Sequencing by hybridization (SBH) is most efficiently practiced by attaching many probes to a surface to form an array in which the identity of the probe at each site is known. A labeled target DNA or RNA is then hybridized to the array, and the hybridization pattern is examined to determine the identity of all complementary probes in the array. Contrary to the teachings of the prior art, which teaches that mismatched probe/target complexes are not of interest, the present invention provides an analytical method in which the hybridization signal of mismatched probe/target complexes identifies or confirms the identity of the perfectly matched probe/target complexes on the array.

Techniques for sequencing a nucleic acid using a probe array have been disclosed in PCT Application No. 92/10588, which is hereby incorporated by reference. Each probe is located at a positionally distinguishable location on the substrate. When the labeled target is exposed to the substrate, it binds at locations that contain complementary nucleotide sequences. Through knowledge of the sequence of the probes at the binding locations, one can determine the nucleotide sequence of the target nucleic acid. The technique is particularly efficient when very large arrays of nucleic acid probes are utilized.

In a preferred embodiment, the device consists of a detection chip having the microfluidic structures needed to release the nucleic acid molecules from a sample. The nucleic acid molecules are introduced into a chamber with the detection system having the probes. The detection switches are connected to a processor which can analyze the results from the hybridization reactions. A user interface, such as a screen is provided for the user to read the results. In addition, the device may have additional information in memory or accessible by modem regarding the organism or individual from which the target nucleic acid molecule was derived.

EXAMPLES

Example 1

Preparation of a Sample to Detect Pathogens

A sample to be tested is isolated. A common sample would be a blood sample from a patient. The sample is injected into the device. The sample moves into a chamber where it is treated chemically, with detergents, and enzymatically, with proteases to free nucleic acid molecules from cells in the sample. Heat treatment is also used to facilitate the release of the nucleic acid molecules. For that reason, proteins used in the present invention are preferably thermostable.

The mixture may then pass though a filter on the chip to partially purify the nucleic acid molecules.

Example 2

Preparation of Oligonucleotide Probe Sets

Each oligonucleotide probe set is selected so that the two probes are complimentary to a portion of the target nucleic acid molecule and so that the two portions of the target nucleic acid molecule are located sufficiently far apart that the nucleic acid molecule can bridge the gap between the two probes on the device when they are both bound. The complimentary sequences will be chosen such that there is some additional length to allow the target nucleic acid molecule to move freely when bound by one probe, so that it may access the second probe. Preferably the molecule will not be much longer than needed to easily bridge the gap. As the length of the molecule increases the chance of it locating the second probe decreases, because the effective concentration of the binding site on the target molecule decreases as the volume in which it can move increases.

Each probe set will be attached to a substrate so that they are positioned as discussed above.

Example 3

Testing for the Presence of the Target Nucleic Acid Molecule

The probe sets will be contacted with the nucleic acid molecules. The test chamber has a small volume to facilitate binding of the target to the probe. To increase the chance of binding, the sample is circulated multiple times through the test chamber. The sample will flow through a test chamber containing the probe sets, at a flow rate sufficiently low to allow the target nucleic acid molecules to bind to a probe. Conditions are determined by the length and sequence of the probe.

The conditions will be set at a level where the stringency is sufficient to eliminate non-specific binding to the probes. The target nucleic acid molecule is contacted with the probes under stringent conditions. The stringent conditions for hybridization are by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions. One or more factors be may be varied to generate conditions of either low or high stringency different from, but equivalent to, the above listed conditions.

The test chamber is then rinsed with a solution to remove unbound nucleic acid molecules. A solution which is non-conducting lowers the level of false positives by cutting down on conductivity mediated by the buffer.

A current is then applied at one lead while a detector looks for a signal at the other lead. A current between the two leads is indicative of the presence of the target nucleic acid molecule.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for detecting a target nucleic acid molecule in a sample, said method comprising:

providing a device for detecting the presence of a target nucleic acid molecule in a sample, comprising:
two electrical conductors, including a first electrical conductor and a second electrical conductor, but where the electrical conductors are not in contact, and one or more sets of two oligonucleotide probes attached to the electrical conductors, where the oligonucleotide probes are positioned such that the probes cannot come into contact with one another and such that a target nucleic acid molecule, which has two sequences, a first sequence complementary to a first probe attached to the first electrical conductor and a second sequence complementary to a second probe attached to the second electrical conductor, can be bound to both probes concurrently;

contacting the probes with a sample which may have the target nucleic acid molecule under selective hybridization conditions to permit target nucleic acid molecules, if any, present in the sample to hybridize to both of the probes;

filling the oligonucleotide probes and the selectively hybridized target nucleic acid molecule with a filling nucleic acid sequence, wherein the filling nucleic acid sequence is complementary to the target nucleic acid molecule and extends between the pair of oligonucleotide probes;

coating the oligonucleotide probes as well as any target nucleic acid molecule, and any filling nucleic acid sequence with a conductor; and determining if an electrical current can be carried between the probes, said electrical current between the probes indicating the presence of the target nucleic acid molecule in the sample which has sequences complementary to the probes.

2. The method according to claim 1, wherein the nucleic acid molecule is DNA.

3. The method according to claim 1, wherein the nucleic acid molecule is RNA.

4. The method according to claim 1, wherein the conductor is silver.

5. The method according to claim 1, wherein the conductor is gold.

6. The method according to claim 1 further comprising:
contacting the target nucleic acid molecule with nucleases after binding with the probes.

7. The method according to claim 1 further comprising:
contacting the target nucleic acid molecule with ligase after binding with the probes and
heating the target nucleic acid molecule to a temperature high enough to denature a non-ligated target nucleic acid molecule from the probes.

8. The method according to claim 1, wherein the probes are complementary to sequences from the genetic material of a pathogenic bacteria.

9. The method according to claim 8, wherein the pathogenic bacteria is a biowarfare agent.

10. The method according to claim 8, wherein the pathogenic bacteria is a food borne pathogen.

11. The method according to claim 1, wherein the probes are complementary to sequences from the genetic material of a virus.

12. The method according to claim 1, wherein the probes are complementary to sequences from the genetic material of a human.

13. The method according to claim 1, wherein one or both of the probes has a sequence which is complementary to a sequence having a polymorphism, where the base or bases complementary to the polymorphism are located at an end of the probe distal to conductor.

* * * * *